US00PP08093P

United States Patent [19]

Meilland

[11] Patent Number: Plant 8,093

[45] Date of Patent: Jan. 12, 1993

[54] ROSE PLANT — MEIMATLOR VARIETY

[75] Inventor: Alain A. Meilland, Antibes, France

[73] Assignee: The Conard-Pyle Company, West Grove, Pa.

[21] Appl. No.: 691,083

[22] Filed: Apr. 24, 1991

[30] Foreign Application Priority Data

Jul. 19, 1990 [FR] France ..... 9755

[51] Int. Cl.[5] ..... A01H 5/00

[52] U.S. Cl. ..... Plt./18

[58] Field of Search ..... Plt./11, 18

[56] References Cited

U.S. PATENT DOCUMENTS

P.P. 6,031 10/1987 Marciel ..... Plt. 18

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms with an excellent capacity for reblooming attractive double long lasting blossoms which are Venetian pink in coloration. The new variety originated as a spontaneous mutation of the Devolor variety (U.S. Plant Pat. No. 6,031) and can be readily distinguished from its parent which forms Rhodamine pink blossoms. The plant exhibits an upright growth habit, forms vigorous vegetation, and is well suited for cut flower production in a greenhouse since it forces well. Additionally, the plant is not particularly affected by cryptogamic diseases.

1 Drawing Sheet

SUMMARY OF THE INVENTION

The new variety originated at Cap d'Antibes, France, as a spontaneous sport or mutation of unknown causation which occurred in a plant of the Devolor variety (U.S. Plant Pat. No. 6,031). In the United States the Devolor variety is known as the De Vine variety. The new plant was discovered during the selective study of plants which were newly formed by grafting.

I was attracted to a single plant of the new variety because of its distinctive blossom coloration. More specifically, the plant of the new variety exhibited a Venetian pink blossom coloration while the parent Devolor variety consistently formed the characteristic Rhodamine pink blossoms. Had I not discovered, studied over an extended period of time, and carefully preserved the new variety, it would have been lost to mankind.

It was found that the new variety of Hybrid Tea rose plant of the present invention possesses the following combination of characteristics:

(a) forms in abundance with an excellent capacity for reblooming attractive long lasting double blossoms which are Venetian pink in coloration,
(b) exhibits medium green adult wood,
(c) exhibits vigorous vegetation,
(d) exhibits an upright growth habit,
(f) is particularly suited for forcing in a greenhouse, and
(g) is not particularly affected by cryptogamic diseases.

The new variety well meets the needs of the horticultural industry and is particularly well suited for cut flower production under greenhouse conditions.

The new variety has been found to undergo asexual propagation by a number of routes, including budding, grafting, cuttage, etc. Asexual propagation by the above-mentioned routes as performed in France and the United States has shown that the characteristics of the new variety are strictly transmissible from one generation to another.

The new variety has been named the Meimatlor variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were 18 months of age and were observed during February while growing in a greenhouse at Cap d'Antibes, France.

DETAILED DESCRIPTION

Figures 1, 2, 3, 4, 5, 6, 7, 8, 9, 10, 11, 12, 13, 14, 15:
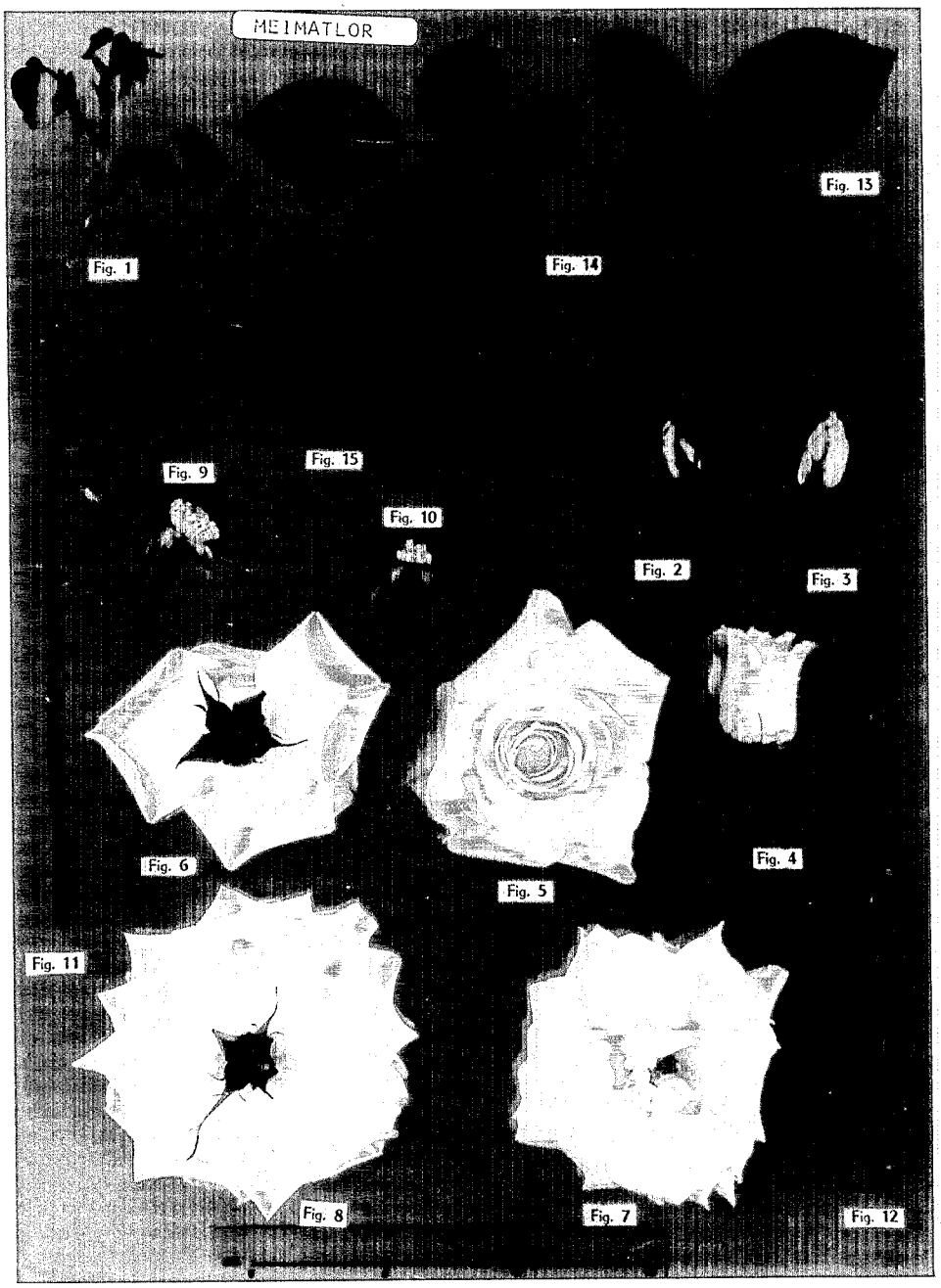
FIG. 1 illustrates a specimen of a young shoot.
FIG. 2 illustrates a specimen of a floral bud at the opening of the sepals.
FIG. 3 illustrates a specimen of a floral bud as the petals begin to open.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower at the end of blooming — plan view — obverse.
FIG. 8 illustrates a specimen of a fully open flower at the end of blooming — plan view — reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of a main branch.
FIG. 13 illustrates specimens of leaves with three leaflets — plan view — upper surface (top), and lower surface (bottom)
FIG. 14 illustrates a specimen of a leaf with five leaflets — plan view — lower surface.
FIG. 15 illustrates a specimen of a leaf with seven leaflets — plan view — under surface.

The chart used in the identification of the colors is that of The Royal Horticultural Society (R.H.S. Colour Chart). The description is based on the observation of 18 month old plants made during February while being grown in a greenhouse at Cap d'Antibes, France. The coloration in common terms precedes reference to the chart.

Class: Hybrid Tea.

Plant:

*Height.*—Approximately 120 cm. on average for budded plants grown for one season, and when plants are cut back to a height of 85 cm., stems commonly are produced having a length of approximately 50 to 90 cm.

*Habit.*—Upright.

Branches:

*Color.*—Young stems: lettuce green, Yellow-Green Group 144A. Adult wood: dark green, Green Group 138B.

*Thorns.*—Size: medium to small. Quantity: few. Color: greenish with reddish base on young stems and greenish changing to tan on adult wood.

Leaves:

*Stipules.*—Adnate, pectinate, not very wide and linear.

*Petioles.*—Upper surface: striped reddish brown on young foliage and medium green on mature foliage with more or less glandular edges. Under surface: light green, bear a few prickles which are mingled with glandular acicules.

*Leaflets.*—Number: 3, 5 (most often), and 7. Shape: elliptic and often exhibit an asymmetric tip. Serration: regular. Texture: leathery. General appearance: dense, with a bright general aspect. Color (young foliage): Upper surface: lettuce green, Yellow-Green Group 144A, more or less suffused with reddish brown. Under surface: lettuce green, Yellow-Green Group 144B, more or less suffused with reddish coloration. Color (adult foliage): Upper surface: medium green, Green Group 137A. Under surface: light green, Green Group 138A.

Inflorescence:

*Number of flowers.*—Usually one single bloom per stem.

*Peduncle.*—Light green, very long, and bears a few glandular appendices. The length is approximately 13 to 17 cm. on average.

*Sepals.*—Upper surface: tomentose, greenish in coloration. Under surface: light green, and the outer sepals have edges which are only slightly appendiculated.

*Buds.*—Shape: oblong. Length: approximately 3.5 to 4 cm. on average. Size: large. Color upon opening: Upper surface: pale Venetian pink, Red Group 49D, suffused with light Venetian pink, Red Group 49C. Under surface: pale Venetian pink, Red Group 49D, suffused with light Venetian pink, Red Group 49C.

*Flower.*—Shape: cup-like and fully double. Diameter: approximately 12 to 13 cm. on average. Color (when opening begins): Upper surface: pale Venetian pink, Red Group 49D, suffused with light Venetian pink, Red Group 49C. Under surface: pale Venetian pink, Red Group 49D, suffused with light Venetian pink, Red Group 49C. Color (when blooming): Upper surface: pale Venetian pink, Red Group 49D, suffused with light Venetian pink, Red Group 49C, and turning white on the outer petals. Under surface: pale Venetian pink, Red Group 49D, suffused with light Venetian pink, Red Group 49C, and turning white on the outer petals. Color (at end of opening): Upper surface: pale Venetian pink, Red Group 49D, suffused with light Venetian pink, Red Group 49C, and turning white on the outer petals. Under surface: pale Venetian pink, Red Group 49D, suffused with light Venetian pink, Red Group 49C, and turning white on the outer petals. Fragrance: none. Lasting quality: long lasting when cut and placed in a vase. Petal number: approximately 24 to 30 on average. Petal shape: somewhat flattened. Texture: consistent. Petal drop: good. Stamen number: approximately 185 to 190 on average. Anthers: bright ochre, normal. Filaments: yellowish in coloration, of irregular heights. Pistils: approximately 158 to 163 on average. Stigmas: normal, straw colored. Styles: light fuschia, tomentose near base, and very short. Receptacle: smooth, light green in coloration, and in longitudinal section it is wide and in the shape of a pitcher.

Development:

*Vegetation.*—Vigorous.

*Blooming.*—Excellent.

*Aptitude to be forced in a greenhouse.*—Excellent.

*Resistance to diseases.*—Good.

I claim:

1. A new and distinct variety of Hybrid Tea rose plant characterized by the following combination of characteristics:

(a) forms in abundance with an excellent capacity for reblooming attractive long lasting double blossoms which are Venetian pink in coloration,
(b) exhibits medium green adult wood,
(c) exhibits vigorous vegetation,
(d) exhibits an upright growth habit,
(f) is particularly suited for forcing in a greenhouse, and
(g) is not particularly affected by cryptogamic diseases;

substantially as herein shown and described.

* * * * *

MEIMATLOR